United States Patent [19]

Dyakov et al.

[11] Patent Number: 4,710,196
[45] Date of Patent: Dec. 1, 1987

[54] INTRAOCULAR CRYSTALLINE LENS

[75] Inventors: Nikola G. Dyakov; Pravoslava T. Guguchkova-Yanchuleva; Dimiter V. Benchev, all of Sofia, Bulgaria

[73] Assignee: V T P "Maimex", Sofia, Bulgaria

[21] Appl. No.: 776,787

[22] PCT Filed: Jan. 4, 1985

[86] PCT No.: PCT/BG85/00001
§ 371 Date: Sep. 5, 1985
§ 102(e) Date: Sep. 5, 1985

[87] PCT Pub. No.: WO85/02995
PCT Pub. Date: Jul. 18, 1985

[30] Foreign Application Priority Data

Jan. 5, 1984 [BG] Bulgaria .................................. 63804

[51] Int. Cl.$^4$ .............................................. A61F 2/16
[52] U.S. Cl. ...................................................... 623/6
[58] Field of Search ........................................... 623/6

[56] References Cited
U.S. PATENT DOCUMENTS 4,328,595 5/1982 Sheets ...................................... 623/6
4,435,855 3/1984 Pannu ...................................... 623/6
4,502,162 3/1985 Gerhard et al. ........................ 623/6
4,503,570 3/1985 Grendahh ............................... 623/6
4,588,405 5/1986 Nuolle .................................... 623/6
4,610,689 9/1986 Graether ................................. 623/6

OTHER PUBLICATIONS

American Medical Optics PC-80 Style Sheet, Sep. 1982.

Primary Examiner—Richard J. Apley
Assistant Examiner—James Prizant
Attorney, Agent, or Firm—Karl F. Ross; Herbert Dubno

[57] ABSTRACT

An intraocular crystalline lens to be used for intraocular correction of operational aphasia after the removal of the opaque natural crystalline lens. The intraocular crystalline lens comprises a lenticular body with frontal and lateral apertures and, parallel to one another. The lenticular body is connected with two identical and symmetrically elastic asymmetric elements which come from the lenticular body for contact with the supporting eye surface having two parallel straight extreme parts, the ends of which are inserted in the apertures of the lenticular body.

2 Claims, 3 Drawing Figures 4,710,196

INTRAOCULAR CRYSTALLINE LENS

CROSS-REFERENCE TO RELATED APPLICATIONS

This application is a National Phase corresponding to PCT/BG85/0001, filed Jan. 4, 1985 and based, in turn, upon a Bulgarian application 63804 filed Jan. 5, 1984 under the International Convention.

This invention relates to an intraocular crystalline lens and can be used in medicine for intraocular correction of operational aphalsia after extraction of the opaque natural crystalline lens.

BACKGROUND OF THE INVENTION

An intraocular crystalline lens is known (see U.K. Pat. No. 2,118,841) which comprises a lenticular body with frontal and lateral apertures which are parallel to one another. The lenticular body is connected with two identical elastic asymmetric elements which are symmetrically disposed with respect to the center of the body, these elements extending from the lenticular body for contact with the supporting eye surface. The asymmetric elements have two parallel extreme parts, the ends of which are inserted in the lateral apertures of the lenticular body. Each elastic element consists of three consecutively connected sectors of which the middle one is supporting and the remaining two are connecting. The supporting sector consists of two steps which are separated by a concave arc.

A disadvantage of the known crystalline lens is the small length and the low elasticity of the connecting sectors which determine the total elasticity of the asymmetric element. Another shortcoming is that the two connecting sectors have a different elasticity and the supporting sector hence is not pressed equally on both sides to the supporting eye surface so that in the one step is obtained a greater pressure. This leads to damages to the supporting eye tissues, loss of cellules and decentrating of the crystalline lens in the eye.

OBJECT OF THE INVENTION

The object of the invention is to provide an intraocular crystalline lens which is stable, easily implanted, readily centered and which also has supporting elements which are of high elasticity.

SUMMARY OF THE INVENTION

This object is attained by an intraocular crystalline lens comprising a lenticular body with parallel frontal and lateral apertures whereby the lenticular body has two identical elastic asymmetric elements symmetrically disposed in respect of the center of the body and extending from the lenticular body for contact with a supporting eye surface. The elements each have two parallel straight extreme parts whose ends are inserted in the lateral apertures of the lenticular body whereby each elastic asymmetric element is composed of three adjoining sectors in succession, the middle sector being supporting while the other two are connecting.

According to the invention the supporting sector consists of a widening or bight and a supporting curve. The widening comprises an arc with a radius from 0.30 to 0.90 mm while the supporting curve is so formed that it can be engaged in an enveloping circumference with radius R equal to the radius of the supporting eye surface. The enveloping circumference is intersected by a concentric to the periphery of the lenticular body circumference with radius R equal to the radius of the enveloping circumference whereby between the plotted tangents to these circumferences through their point of intersection is formed an angle alpha from 1.5° to 7.5° and so that the connecting sectors have an equal easticity.

The supporting curve is formed by an arc with radius R equal to the radius of the supporting eye surface.

The supporting curve is formed as wavy and has at least two concave and convex parts.

The connecting sectors have the same form comprising an arc, the one end of which is connected with the supporting sector and the other—with the straight extreme part of the elastic element whereby both parallel extreme parts of the elastic element are disposed in one quadrant.

One of the connecting sectors has an elastic part composed of an elastic arc with central angle greater than 170°. This elastic arc is connected is connected by means of arms respectively with the widening and with the straight extreme part of the elastic element whereby both extreme parallel straight parts of the elastic element are located in two adjacent quadrants.

The advantages of the invention are: high stability, precise centering of the optical part and ease of implanting of the intraocular crystalline lens; great elasticity of the asymmetric elements and maximal adaptation of the intraocular crystalline lens with respect to the supporting eye surface due to the fact that the connecting sectors have equal elasticities and press bilaterally against the supporting sector with the same force.

Figure 1:
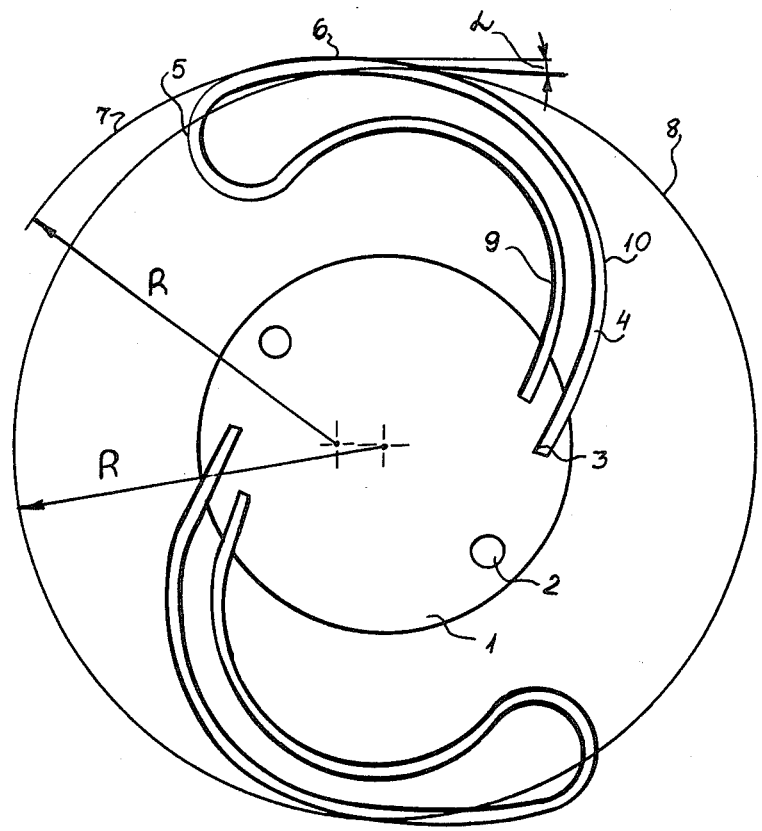
FIG. 1 is a diagrammatic elevational view of an intraocular lens for back chamber implantation.

In the embodiment of an intraocular crystalline lens shown in FIG. 1, the intraocular crystalline lens, preferably for back chamber implanting, comprises a lenticular body 1 which has frontal apertures 2 and parallel between them lateral apertures 3. Extending from the lenticular body 1 are two identical elastic asymmetric elements 4, symmetrically disposed in respect of the center of the lenticular body 1 having parallel straight parts, the ends of which are inserted in the lateral apertures 3 of lenticular body 1. Each elastic element 4 is composed by three consecutively connected sectors, the middle one of which is supporting while the remaining two 9 and 10 are connecting. The supporting sector comprises a widening or bight 5 with radius 0.63 mm and supporting arc 6 which has an enveloping circumferences 7 whose radius R is equal to the radius of the supporting eye surface. The enveloping circumference 7 is intersected by a concentric to the lenticular body 1 circumference 8 with with radius R is equal to the radius of the supporting eye surface. Between the plotted tangents to these circumferences 7 and 8 in their point of intersection is formed an angle alpha equal to 7°30′. The connecting sectors 9 and 10 have the same form, comprising an arc, the one end of which is connected with the widening 5 while the other is connected with the straight extreme part of elastic element 4 whereby both parallel extreme parts of elastic element 4, laying in the lateral apertures 3 of the lenticular body 1 are located in one quadrant with respect to the center of the lens.

Figure 2:
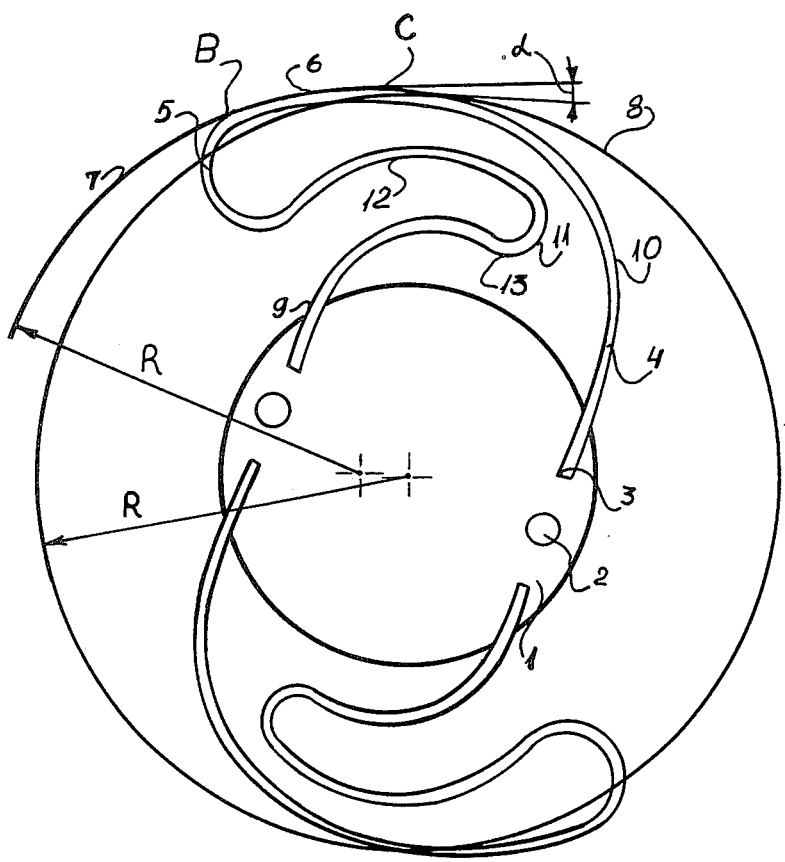
FIG. 2 is a diagrammatic elevational view of a second embodiment of an intraocular lens for back chamber implantation.

A second exemplary embodiment of an intraocular crystalline lens is shown in FIG. 2, representing a view of an intraocular crystalline lens with preferred back chamber intracapsular implanting.

The intraocular crystalline lens for back chamber intracapsular implanting comprises a lenticular body 1 which has frontal apertures 2 and mutually parallel lateral apertures 3. These lateral apertures 3 are disposed in two adjacent quadrants. From the lenticular body 1 extend two identical elastic elements 4 symmetrically disposed with respect to the center of the lenticular body 1 having extreme parallel straight parts the ends of which are inserted in the lateral apertures 3 of the lenticular body 1. Each elastic asymmetric element 4 is composed of three consecutively connected sectors, one of which is supporting while the other two are connecting 9 and 10. The supporting sector comprises a widening 5 with radius 0.56 mm and supporting arc 6 which has an enveloping circumference 7 with radius R equal to the radius of the supporting eye surface whereby the enveloping circumference 7 is intersected by a concentric to the periphery of the lenticular body 1 circumference 8 with radius R equal to the radius of the supporting eye surface. An angle alpha=3°26' is formed at the point of intersection between tangents to these circumferences. One of the continuously curved connecting sectors 10 comprises only one arc which is connected with the straight extreme part of the elastic element 4. The other connecting sector 9 comprises an elastic part composed of arc 11 with a central angle of 194° which is connected by means of 12 and 13 respectively with widening or bight 5 and the other straight extreme part of the elastic element 4. Both straight extreme parts of elastic element 4 are maximally remote one from another and are disposed in two adjacent quadrants of lenticular body 1.

Figure 3:
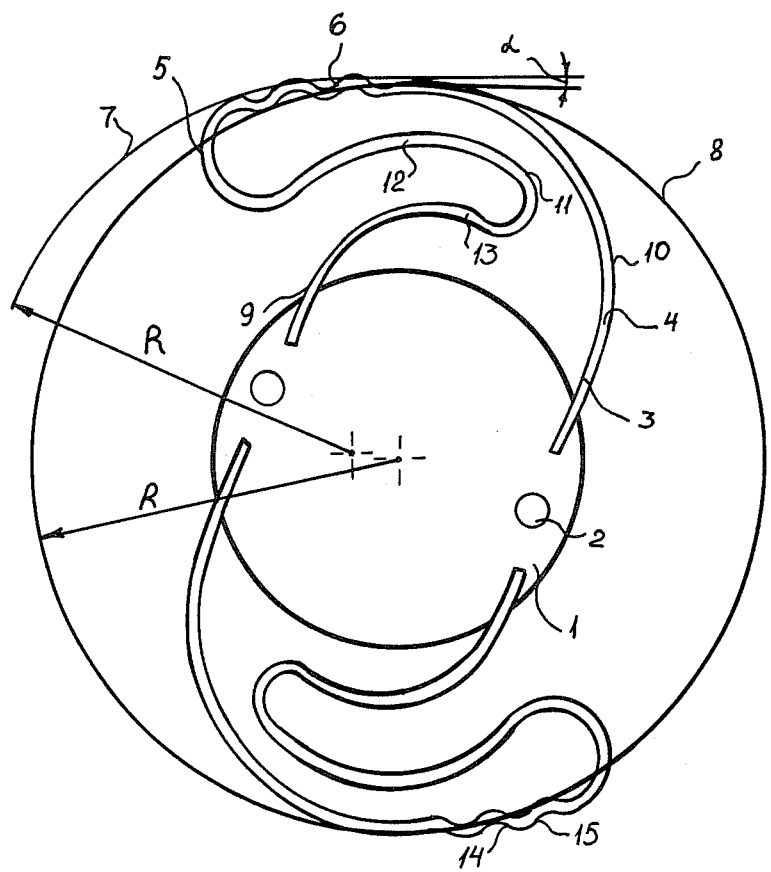
FIG. 3 is another diagrammatic elevational view of an intraocular lens for front chamber implantation.

A third exemplary embodiment of intraocular crystalline lens is shown in FIG. 3, representing a view of an intraocular crystalline lens with preferred front chamber implanting.

The intraocular crystalline lens comprises a lenticular body 1 having frontal apertures 2 and parallel between them lateral apertures 3. From the lenticular body 1 extend two identical elastic asymmetric elements or loops 4 which have parallel straight parts, the ends of which are inserted in the lateral apertures 3 of lenticular body 1. Each elastic asymmetric element 4 is composed of three consecutively connected sectors, the middle one being supporting and the remaining two sectors 9 and 10 are connecting. The supporting sector comprises a widening or bight 5 with radius 0.6 mm and a supporting curve 6. The latter is formed with a wavy shape having two convex and concave parts 15, 14 as well as an enveloping circumference 7 with radius R equal to the radius of the supporting eye surface whereby the enveloping circumference 7 is intersected by a concentric to the lenticular body 1 circumference 8 with the same radius. Between the plotted tangents to these circumferences is formed in their point of intersection an angle alpha=2°48'. One of the connecting sectors 10 comprises an arc which is connected with the straight extreme part of the elastic element 4. The other connecting sector 9 comprises an elastic part composed of arc 11 with a central angle of 198°, which is connected by means of arms 12 and 13 respectively with the widening or bight 5 and with the straight extreme part of elastic element 4. Both straight extreme parts of elastic element 4 are maximally remote one from another and are disposed in two adjacent quadrants of lenticular body 1.

Upon implanting of the intraocular crystalline lens in the eye, the supporting curve 6, is rotated due to deformation of the connecting sectors 9 and 10 which is caused by the forces of fixation and centering of the intraocular crystalline lens in the supporting eye surface. Centering is effected concentrically to the periphery of the lenticular body while the pressing forces on both sides of the supporting sectors are equalized.

We claim:

1. An implantable intraocular lens assembly comprising:
   a circular crystalline lenticular body formed with a pair of mutually parallel frontal apertures traversing opposite lens surfaces, and two pairs of mutually parallel lateral apertures opening along the circumference of said lenticular body; and
   two asymmetric elastic loops disposed symmetrically with respect to a center of said body for affixing the lens assembly to and eye surface surrounding said assembly, each of said loops:
   having respective mutually parallel straight portions received in the lateral apertures of a respective one of said pairs,
   being continuously curved between said straight portions,
   having outwardly convexly curved inner and outer portions diverging toward a bight in the form of a circular arc segment with a radius of 0.3 to 0.8 mm with said outer portion being progressively of increasing spacing from said circumference away from a respective straight portion and constituting a supporting sector engageable with said eye surface,
   being so formed with said supporting sector that said supporting sector has an enveloping circumference with a radius of curvature R equal to that of said eye surface and intersected by a circle concentric with said body such that tangents to said circle and enveloping circumference at a point of intersection include an angle of 1.5° to 7.5°,
   being constructed so that said supporting sector and said bight are connected respectively by connecting sectors to said straight portions, said connecting sectors having the same elasticity, and
   said supporting sector has a wavy configuration with at least two outwardly convex parts alternating with at least two outwardly concave parts.

2. The implantable intraocular lens assembly defined in claim 1 wherein
   said straight portions of each loop are widely spaced and each straight portion lies in the same quadrant as the straight portion of the other loop with respect to the center of said body, and
   said inner portion of each loop is formed with a further bight approaching the outer portion thereof.

* * * * *